(12) United States Patent
Grier et al.

(10) Patent No.: US 7,137,574 B2
(45) Date of Patent: Nov. 21, 2006

(54) APPARATUS AND PROCESS FOR THE LATERAL DEFLECTION AND SEPARATION OF FLOWING PARTICLES BY A STATIC ARRAY OF OPTICAL TWEEZERS

(75) Inventors: David G. Grier, New York City, NY (US); Pamela T. Korda, Los Angeles, CA (US)

(73) Assignee: University of Chicago, Chicago, IL (US)

( * ) Notice: Subject to any disclaimer, the term of this patent is extended or adjusted under 35 U.S.C. 154(b) by 94 days.

(21) Appl. No.: 10/878,797

(22) Filed: Jun. 28, 2004

(65) Prior Publication Data

US 2005/0001063 A1    Jan. 6, 2005

Related U.S. Application Data

(63) Continuation of application No. 09/951,117, filed on Sep. 13, 2001, now Pat. No. 6,797,942.

(51) Int. Cl.
B05B 1/26 (2006.01)
B05B 1/34 (2006.01)
B05B 1/30 (2006.01)

(52) U.S. Cl. ............... 239/461; 239/463; 239/464; 239/466; 239/467; 239/513

(58) Field of Classification Search ............... 239/461, 239/463, 464, 466, 467, 483, 503, 513; 250/251; 359/566

See application file for complete search history.

(56) References Cited

U.S. PATENT DOCUMENTS

| | | | |
|---|---|---|---|
| 3,710,279 A | 1/1973 | Ashkin | |
| 5,495,105 A | 2/1996 | Nishimura et al. | |
| 5,512,745 A * | 4/1996 | Finer et al. | 250/251 |
| 5,939,716 A | 8/1999 | Neal | |
| 6,055,106 A | 4/2000 | Grier et al. | |
| 6,797,942 B1 * | 9/2004 | Grier et al. | 250/251 |
| 6,815,664 B1 | 11/2004 | Wang et al. | |
| 2002/0181837 A1 | 12/2002 | Wang et al. | |
| 2003/0007894 A1 | 1/2003 | Wang et al. | |
| 2005/0094232 A1 | 5/2005 | Kibar | |
| 2005/0164372 A1 | 7/2005 | Kibar | |

FOREIGN PATENT DOCUMENTS

| | | |
|---|---|---|
| DE | 19952322 | 5/2001 |
| WO | WO 0239104 | 5/2002 |

* cited by examiner

Primary Examiner—Davis Hwu
(74) Attorney, Agent, or Firm—Foley & Lardner LLP

(57) ABSTRACT

A method and apparatus for laterally deflecting and/or separating a flow of particles using a static array of optical tweezers. In an array of optical tweezers with a lattice constant larger than the size of a particle of interest, particles driven past the array by an external force experience an additional interaction with the array of traps. By altering the angle of the array of traps relative to the external force, the particles' movement from trap to trap inside the array can be biased away from the direction of the external force, thereby enabling selective deflection and/or separation of particles.

12 Claims, 10 Drawing Sheets

APPARATUS AND PROCESS FOR THE LATERAL DEFLECTION AND SEPARATION OF FLOWING PARTICLES BY A STATIC ARRAY OF OPTICAL TWEEZERS

CROSS-REFERENCE TO RELATED PATENT APPLICATIONS

This application is a Continuation of U.S. application Ser. No. 09/951,117, filed Sep. 13, 2001, now U.S. Pat. No. 6,797,942 incorporated herein by reference in its entirety.

This invention was made with U.S. Government support under Grant No. DMR-9730189 awarded by the National Science Foundation and through the MRSEC Program of the National Science Foundation under Grant Number DMR-9880595. The Government has certain rights in this invention.

FIELD OF THE INVENTION

The present invention relates generally to a system and method for achieving a fractionation of particles. More particularly, the present invention relates to a system and method for achieving a lateral fractionation and/or separation of particles through the use of a static array of optical traps

BACKGROUND OF THE INVENTION

A number of techniques are conventionally known that are capable of fractionating particles in limited circumstances. For example, one such technique involves the use of a microfabricated sieve consisting of a two-dimensional lattice of obstacles or barriers for DNA separation. The asymmetric disposition of obstacles or barriers rectifies the Brownian motion of DNA molecules that pass through the sieve, causing the particles to follow paths that depend on the respective diffusion coefficients of the DNA present. Although moderately effective, this technique includes a number of limitations. For example, because the lattice is microfabricated, the overall structure is capable of neither tuning nor adjusting the types and sizes of particles that are fractionated. Furthermore, such lattices tend to suffer from clogging, requiring flushing of the system and restarting.

Further, many conventional techniques for fractionating particles achieve physical separation of the various fractions along the direction of an applied force. For this reason, they operate on discrete batches of samples, and do not operate continuously.

SUMMARY OF THE INVENTION

It is therefore an object of the invention to provide an improved system and method for the lateral deflection of flowing particles that is both tunable and continuous.

It is another object of the invention to provide an improved system and method for laterally deflecting particles that does not become readily clogged with particles.

It is still another object of the invention to provide an improved system and method usable for particle purification and separation.

It is yet another object of the invention to provide an improved system for laterally deflecting particles that can be used for the purification and separation of proteins.

It is another object of the invention to provide an improved system that is capable of physically separating small particles by size, shape, dielectric constant, surface charge density, magnetic susceptibility, nonlinear optical properties, and index of refraction.

It is yet another object of the invention to provide an improved system and method employing a minimal number of moving components for laterally deflecting flowing particles.

It is still another object of the invention to provide an improved system and method for laterally deflecting particles that is usable for the separating of chromosomes.

It is yet another object of the invention to provide for an improved system and method for laterally deflecting particles that can be used for DNA sizing.

It is another object of the invention to provide an improved system and method for laterally deflecting particles that can also be used to purify and/or separate macromolecules and/or nanoclusters or other nanosized material.

Further advantages and features of the present invention will be apparent from the following specification, claims and drawings illustrating the preferred embodiments of the present invention.

DETAILED DESCRIPTION OF THE INVENTION

In order to illustrate embodiments of the invention, an explanation is provided to describe the methodology and function of one embodiment of the present invention. Although the manner in which the phenomenon is described is one rigorous approach which explains the operation of the invention for those skilled in the art, other explanations also can be used to describe similar results which characterize embodiments of the invention. The invention is therefore not limited to the description of its operation by the following specification and drawings.

Figure 1A:
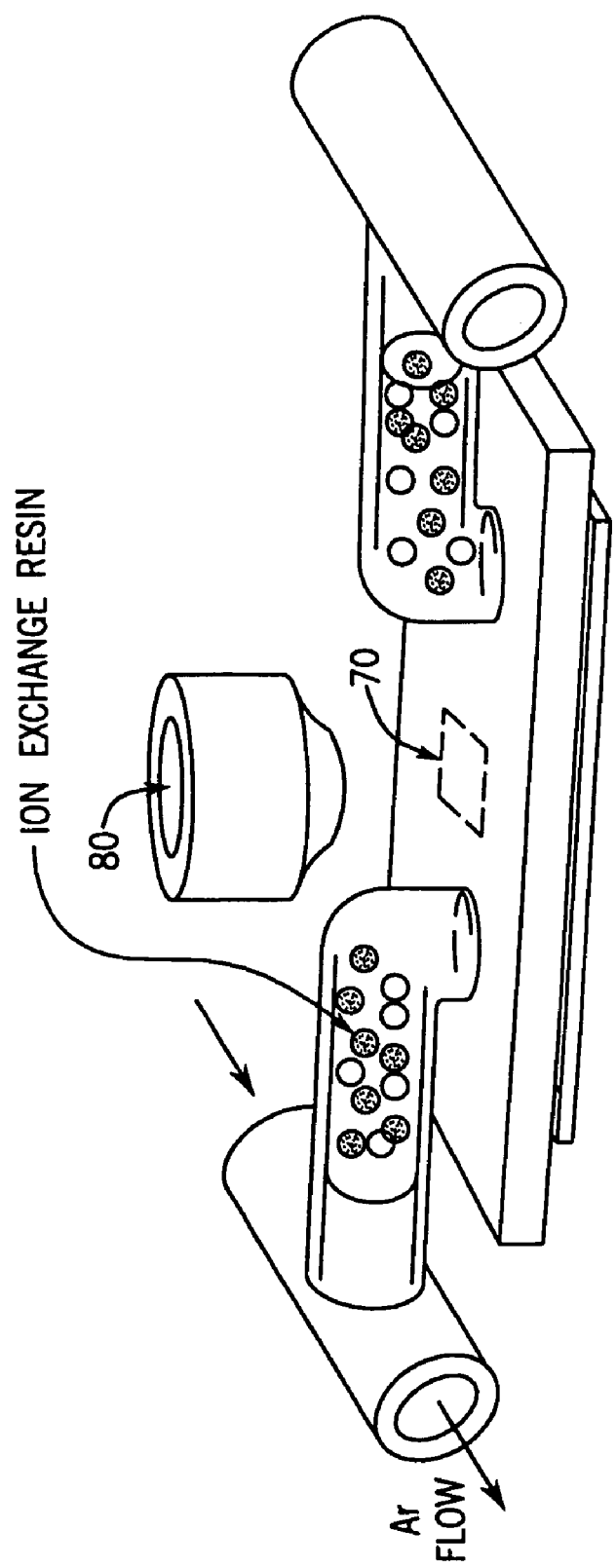
FIG. 1A is a schematic of a holographic optical tweezer system projecting an optical tweezer array onto a flowing colloidal particle suspension.

For a comprehensive understanding of the present invention, it is helpful to consider a holographic optical tweezer system 10 as shown in FIG. 1A and a resulting square array 110 of individual optical tweezers 112. The system 10 includes a laser beam 20 which is passed through a diffractive optical element 30, then processed by relay lens 40, reflected by dichroic mirror 50, and then laser beam 20 is focussed into optical traps by objective lens 60. The optical traps (not shown) are formed in sample chamber 70 and the trapped particle array (not shown) is viewed by a conventional light microscopy system including condenser lens 80, the objective lens 60, a video eyepiece 85 and charge coupled device camera 90.

Figure 1B:
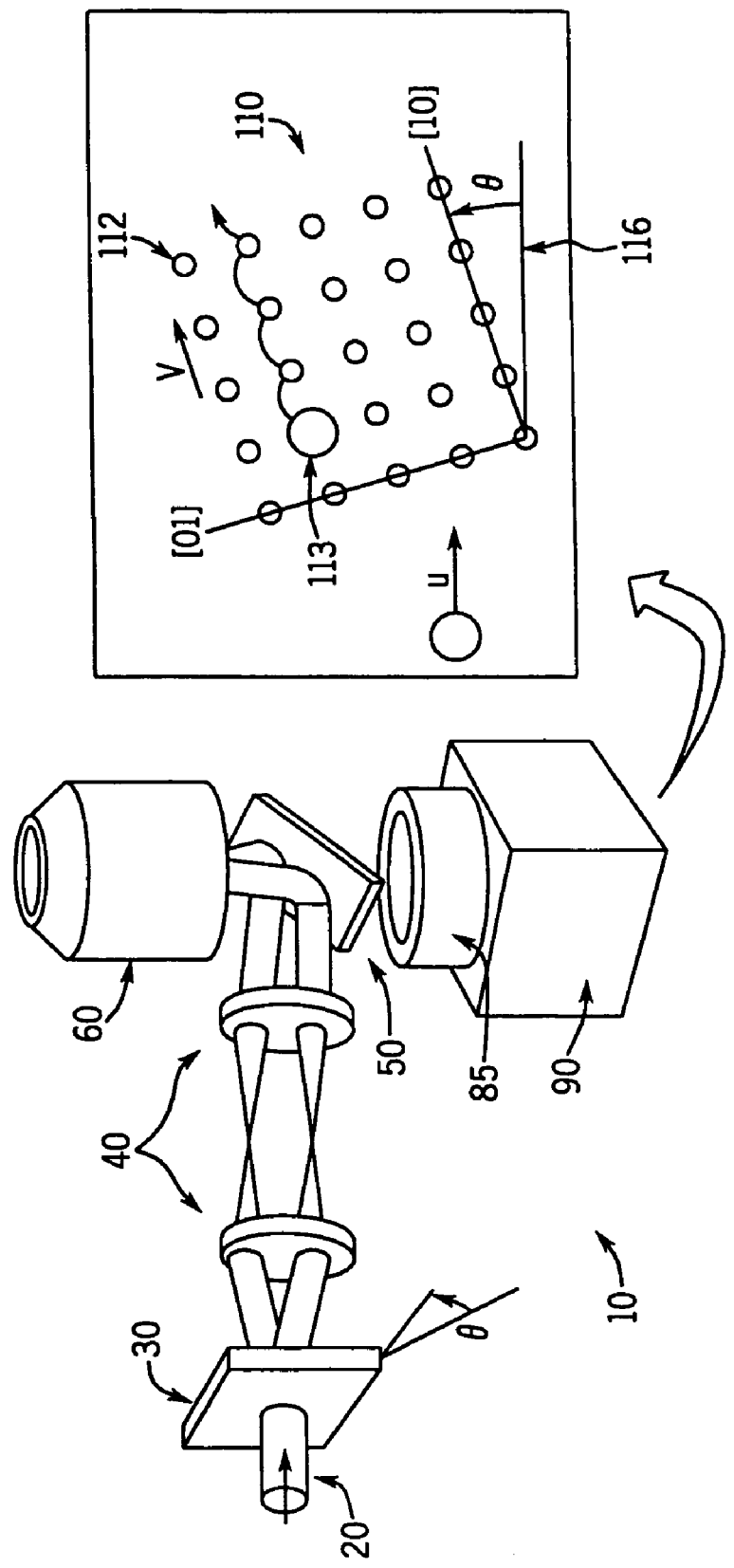
FIG. 1B is a schematic view from the CCD camera of FIG. 1A.

The resulting optical tweezer system 10 generates a square array 110 of individual optical tweezers 112 as shown in FIG. 1B. The optical tweezers 112 exhibit a lattice constant which typically, although not exclusively, has a somewhat larger distance between the optical tweezers 112 than the size of a particle 113 of interest. The particles 113 driven past the array 110 by an external force from a bias source 117 experience an additional interaction with the array 110 of individual traps 112. If the trapping force is considerably greater than the external driving force, the particles 113 will become bound. If, on the other hand, the external force dominates, the particles 113 will flow past the array 110 with their trajectories essentially unperturbed. The preferred embodiment operates in the intermediate regime in which the external force exceeds the trapping force for all of the particles 113 in the sample, but to a differing degree for different fractions of the sample.

Under these conditions, the external force causes the particles 113 to hop from one of the traps 112 to another, occasionally pausing for periods depending on the relative strengths of the optical traps 112 and external force, given the properties of the particular particle 113. If the external force is aligned with the principal axes of the trapping array 110, the resulting hopping trajectories will be aligned with the external force. If, on the other hand, the traps' axes are rotated with respect to the direction of the external force, then the particles' hopping can be biased away from the direction of the external force. Such deflection has been shown in computer simulations of magnetic flux quanta flowing through type-II superconductors and has been inferred indirectly from the appearance of transverse voltage gradients in periodic Josephson junction arrays. The net deflection returns to zero once the array is rotated to 45° for one of two reasons (1) positive and negative displacements can occur with equal probability or (2) the particles jump diagonally through the array, having become locked into the [11] direction.

Figure 1C:
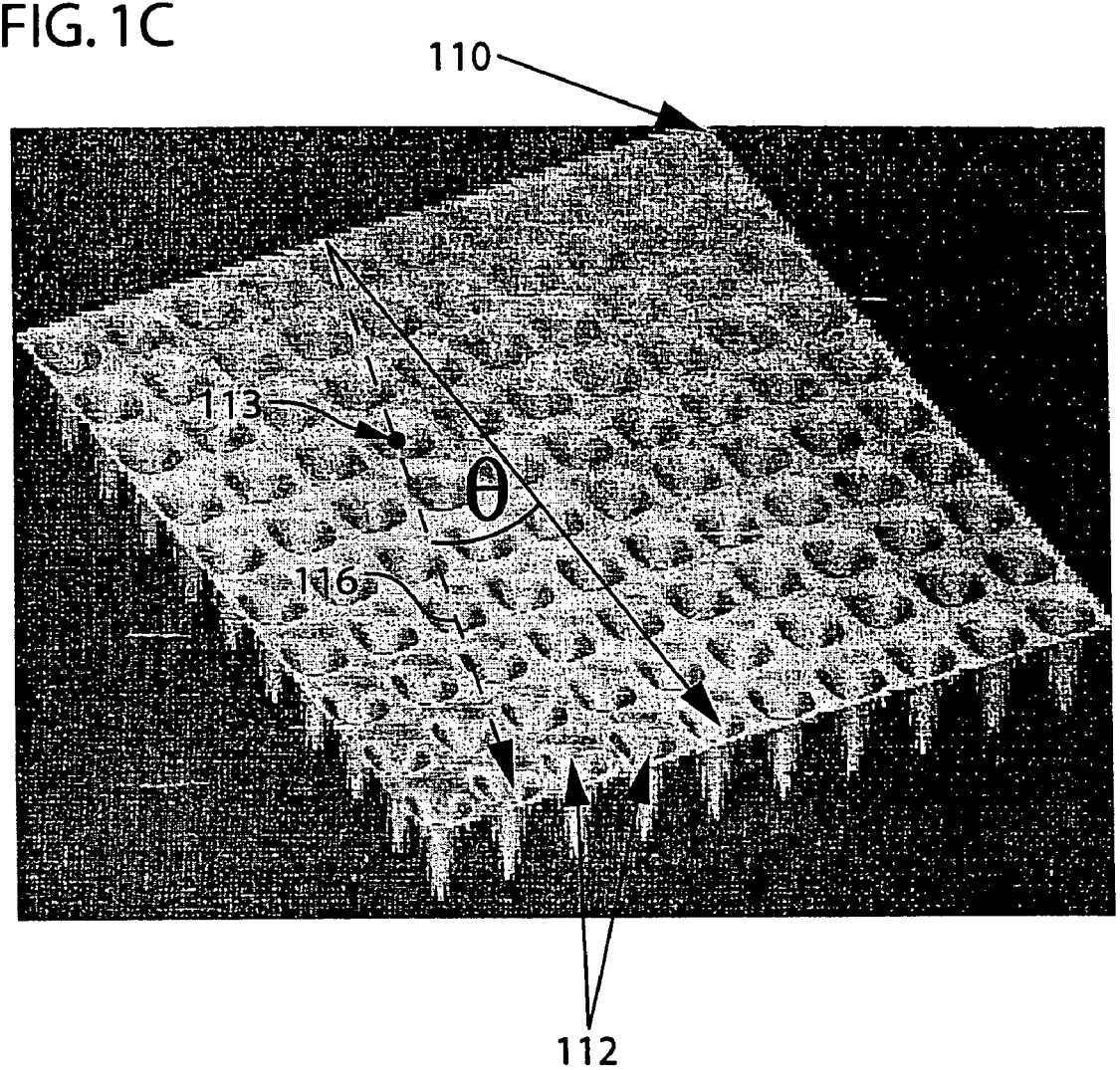
FIG. 1C is a perspective representation of a 10×10 optical tweezer array for laterally deflecting flowing particles in accordance with the present invention.
Figure 3:
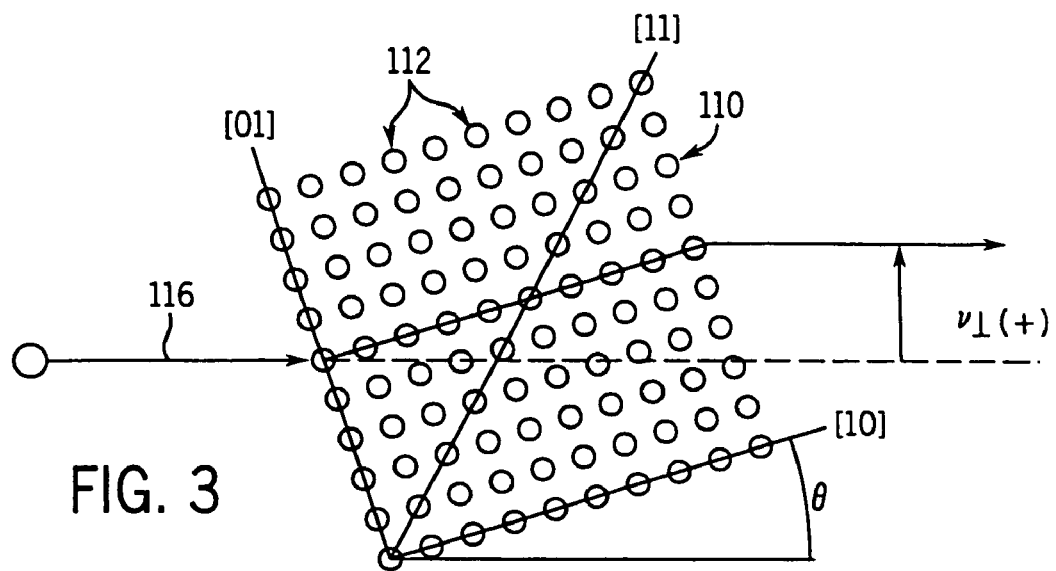
FIG. 3 is a first representation of the movement of individual particles through an array of optical traps offset from the direction of an external force by a tilt angle θ.
Figure 4:
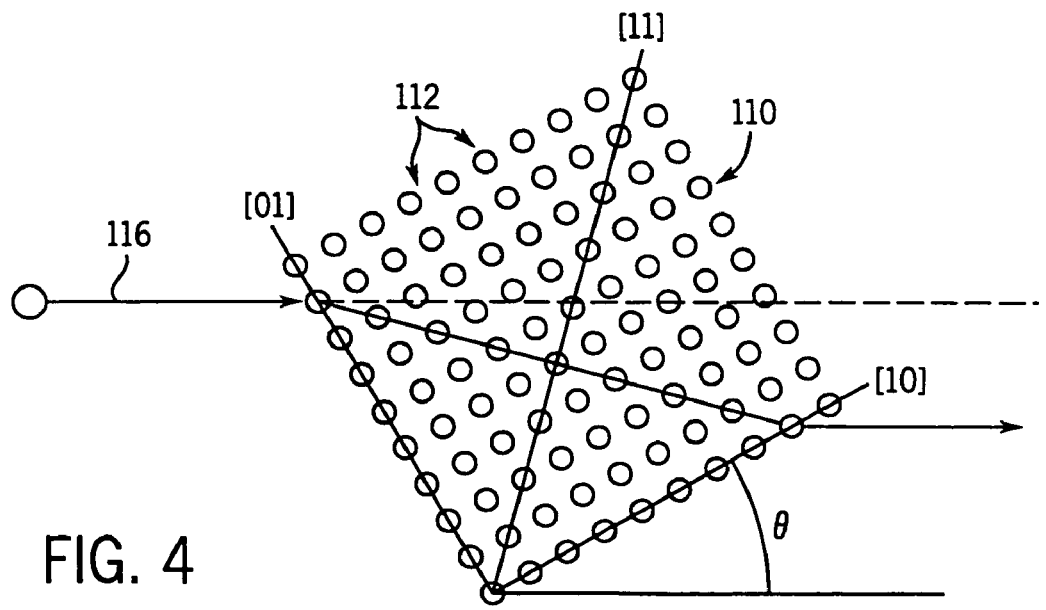
FIG. 4 is a second representation of the movement of individual particles through an array of optical traps offset from the direction of an external force.

FIGS. 3 and 4 are diagrammatic or illustrative general representations of individual particles moving through the array 110 of the traps 112 that has a tilt angle θ relative to the direction of an external bias force 116 (see FIG. 1C also). As can be seen in FIGS. 3 and 4, depending upon the relative tilt angle θ of the array 110, it is possible for the individual particles 113 to be laterally deflected in both positive and negative directions.

Figure 2A:
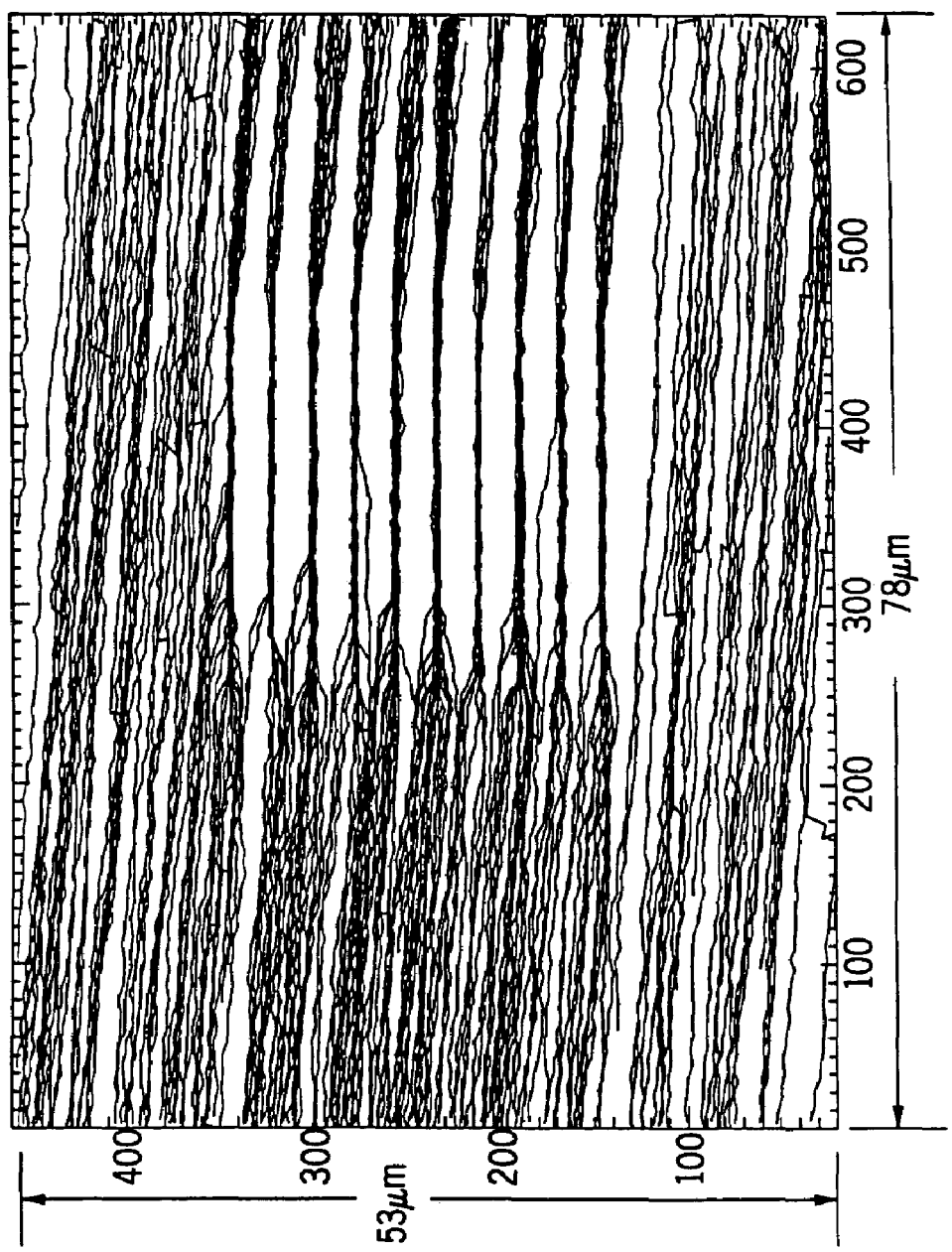
FIG. 2A is a plot showing the channeling of particles through an aligned, 10×10 array of optical tweezers.

FIG. 2A shows an example of utilization of the system 10 with trajectories 115 of 1.5 μm diameter silica, spherically shaped particles 113 passing through the 10×10 array 110 of the optical traps or tweezers 112, with about 2.4 μm of space between each of the tweezers 112. The "y" axis represents about 53 μm, and the "x" axis about 78 μm. In this representation, a pressure gradient is driving the particles 113 from left to right at a speed of about 30 μm/sec. With a substantially zero degree tilt angle for the array 110, the particles 113 are locked into a trajectory (from left to right) with minimal lateral deflection. The measured particle trajectories shown in FIGS. 2A–2D are also oriented with the applied flow directed from left to right.

FIG. 2A therefore shows trajectories of roughly 1000 spheres (the particles 113) with the flow aligned along the [10] lattice direction. The particles 113 are drawn into the rows of the tweezers 112 from an area extending to about 3 μm beyond the array's boundaries, and thereafter follow the [10] rows to their ends. Transverse fluctuations are greatly suppressed by the trapping potential while the particles' longitudinal motion is punctuated only by brief irregular pauses in individual optical potential wells. The time required for the particle 113 to make a transverse jump is so much greater than the longitudinal jump interval that the particles 113 essentially never leave the [10] rows. This influence of the discrete trapping potential on the particles' trajectories constitutes a kinetically locked-in state. Once the particles 113 have hopped through the ranks of the tweezers 112, they return to the bulk flow, their trajectories eventually blurring into each other through diffusion.

Figure 2B:
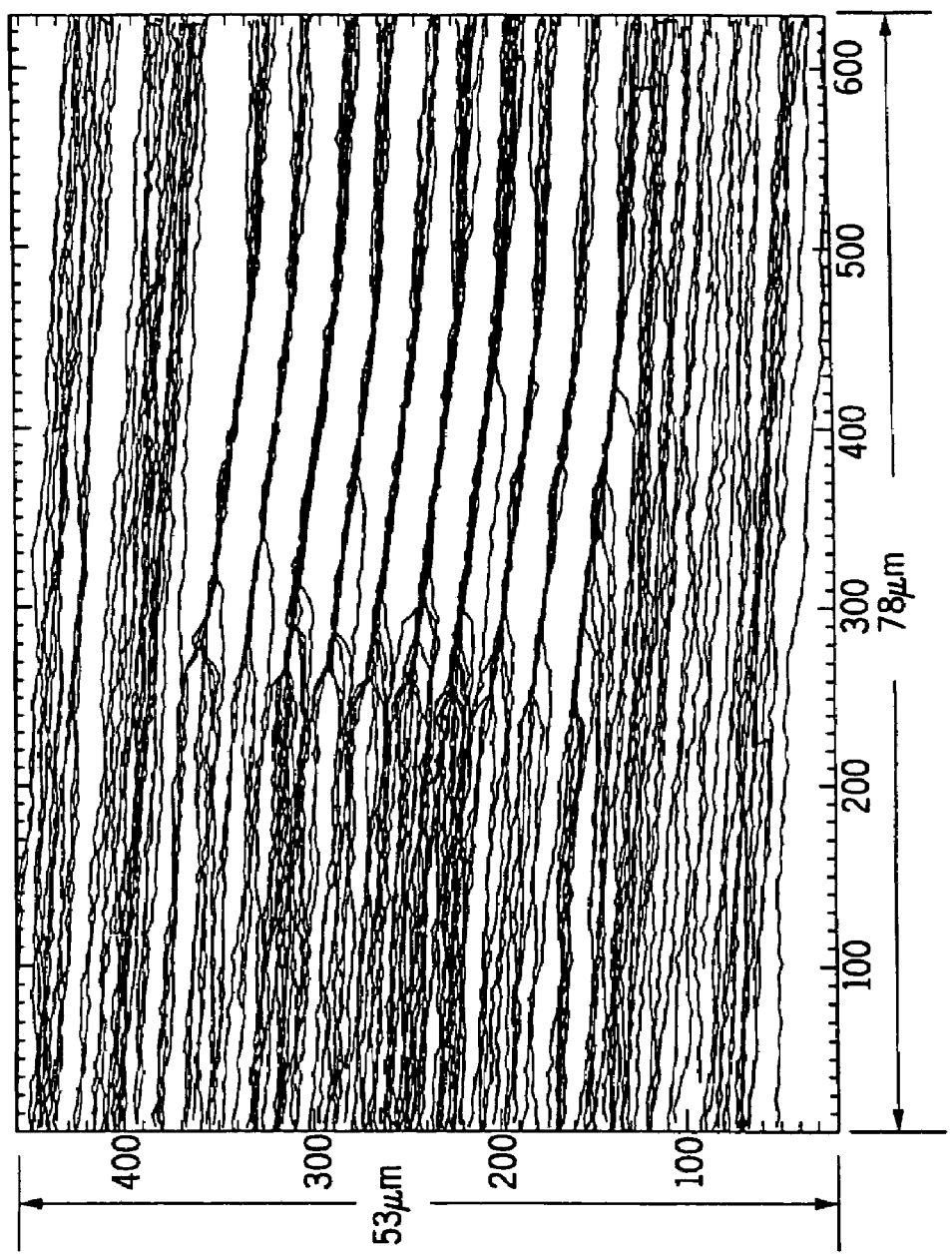
FIG. 2B is a plot showing the trajectories of particles flowing along the axes of a 10×10 array of optical traps oriented at a tilt angle of five degrees relative to the flow direction.

Rotating the diffractive optical element 30 through an angle θ also rotates the pattern of the tweezers 112 with respect to the flow direction without otherwise altering the traps' characteristics. FIG. 2B shows the same sample with the optical tweezers 112 oriented at θ=5° with respect to the flow. As in FIG. 2A, the particles' tracks remain closely locked in to the array's [10] rows. Unlike the example in FIG. 2A, however, the trajectories now are systematically deflected away from the flow's direction. This deflection leaves a distinct shadow on the downstream side of the array into which comparatively few of the particles 113 wander.

Figure 2C:
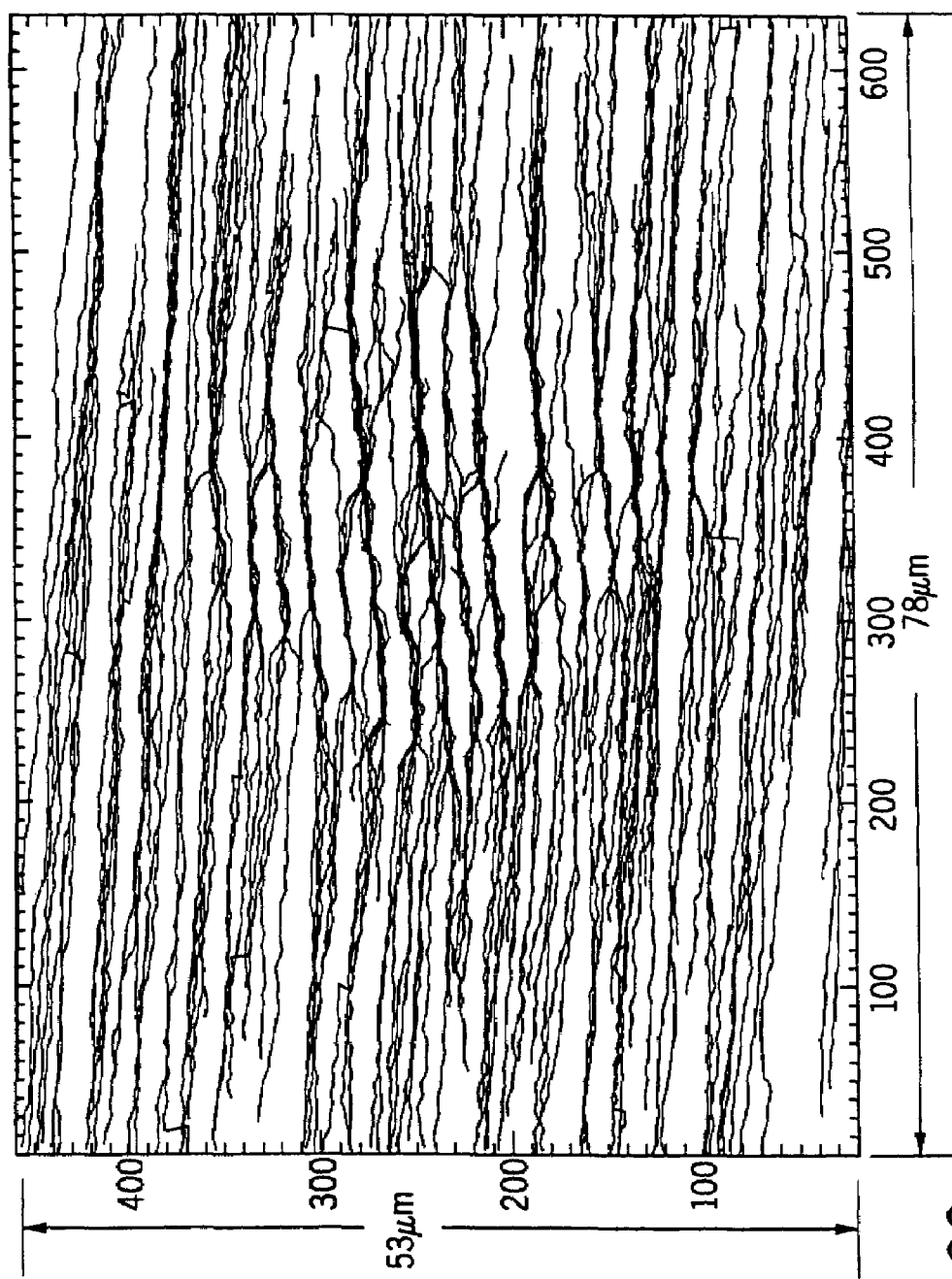
FIG. 2C is a plot showing the trajectories of particles that are laterally deflected by a trap array oriented at a tilt angle of thirty seven degrees with respect to the direction of flow.
Figure 2D:
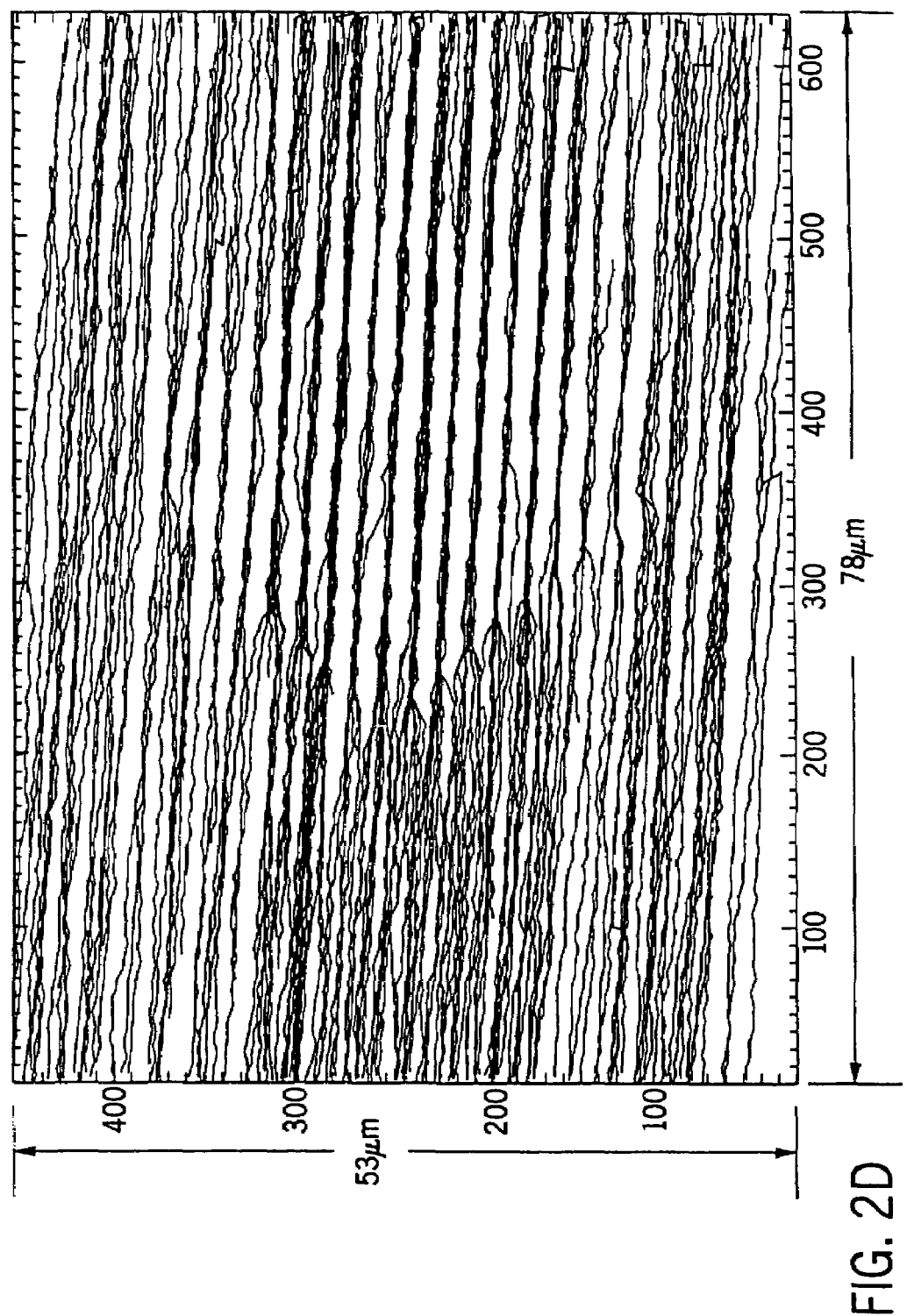
FIG. 2D is a plot showing the substantially undeflected trajectories of particles flowing past an array of traps oriented at a tilt angle of forty-five degrees with respect to the direction of flow.

Further rotation changes the array's influence markedly. FIG. 2C shows the array rotated to θ=37°, with other conditions unchanged. Rather than following the [10] lattice rows to positive deflection, the particles 113 have now locked in to the [11] lattice direction and experience a retrograde deflection. This crossover from [10] to [11] locked-in states reflects the different local potential energy landscape the particle 113 experiences as it is forced along different directions. At some threshold angle beyond the geometrically determined crossover point at 22.5°, the jump rate for [11] hops exceeds that for [10] hops by a large enough margin that the particles 113 become locked in to diagonal trajectories. Rotating still further to θ=45° as in FIG. 2D reduces the degree of deflection while enhancing the trajectories' alignment with the [11] lattice direction.

It is believed that the kinetically locked-in states should form a hierarchy whose influence on transport properties is expected to take the form of a Devil's staircase of plateaus in the longitudinal transport with increasing rotation. Our observation of states locked into the [10] and [11] directions correspond to the principal plateaus of these hierarchies.

We also observe the sign of the transverse deflection to change with monotonically increasing rotation angle θ. This differs from other systems in that no change of sign is predicted for the Hall coefficient of a periodically modulated two-dimensional electron gas with increasing magnetic field. If indeed such sign reversal could be obtained through simple patterning of an electronic system, the effect would be advantageous and could have widespread applications in magnetic data retrieval.

Figure 5:
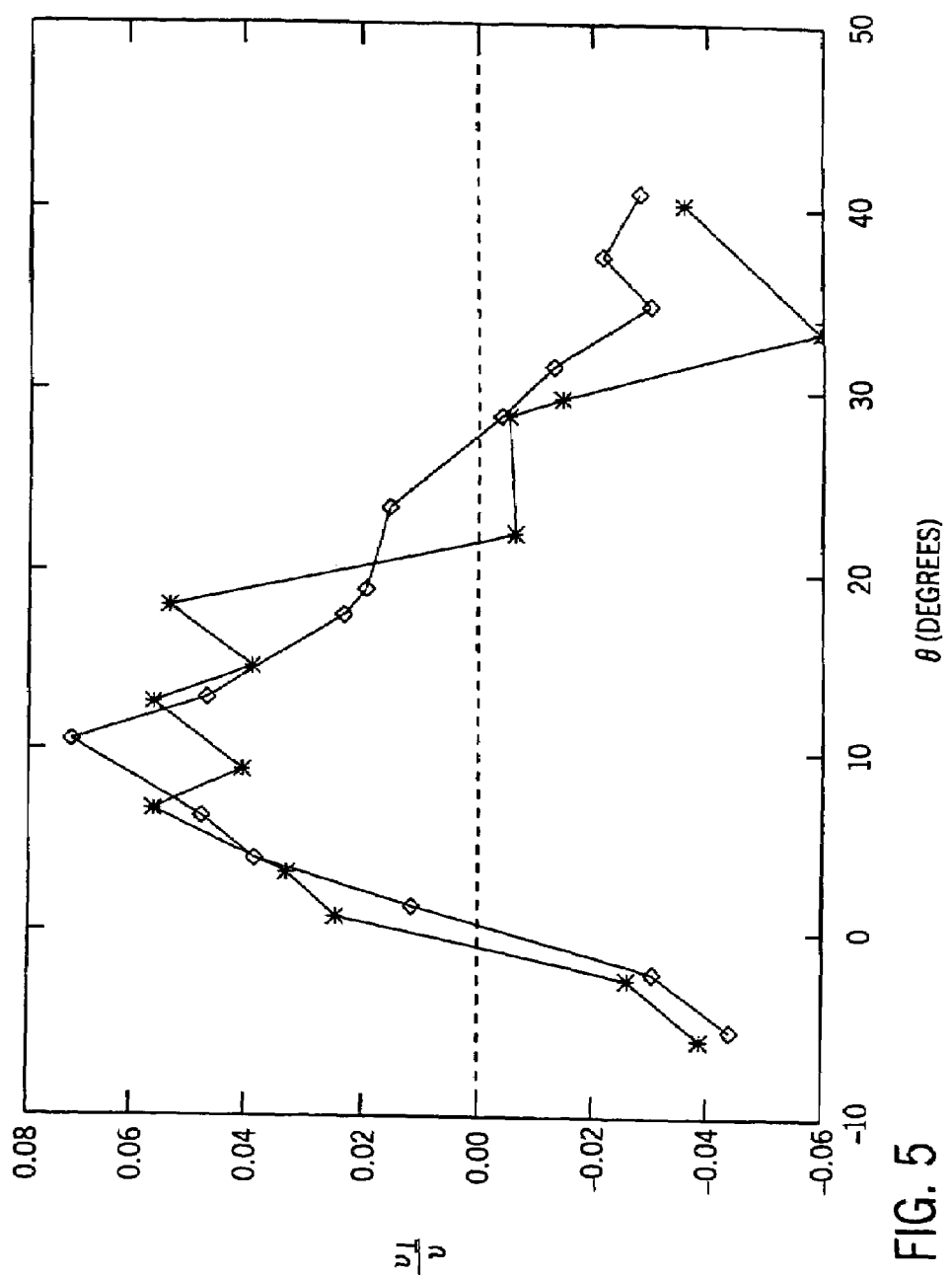
FIG. 5 is a plot showing the ratio of transverse velocity to forward velocity of a particle relative to the angular orientation of the trap array for two different experimental runs under comparable conditions.

FIG. 5, the data points and connecting solid lines represent the relative transverse velocity attained by the particles 113 when the applied and trapping forces they experience in the system 10 are comparably strong. The dashed line, on the other hand, represents the absence of transverse deflection expected for the same particle 113 if the applied force 117 were to dominate the trapping force. FIG. 5 also shows that the amount and direction of lateral deflection can be optimized by changing the rotation angle θ for a given laser power and the external driving force 117. Reducing the laser power would reduce the maximum deflection attainable, with no deflection occurring when the laser 20 is extinguished (See FIG. 1A). As can also be seen in FIG. 5, there is virtually no lateral deflection at all when the tilt angle is θ either 0° or about 22.5°, nor should there be a deflection for θ of about 45°. It should also be noted, however, that there is also no lateral deflection when the tilt angle is about 22.5°. Empirical data has suggested that, for a given particle size and power level, the maximum amount of lateral deflection occurs when as the tilt angle approaches about 17°. When the tilt angle passes about 22.5°, the lateral deflection of the particle 113 changes direction entirely. Empirical data has suggested that the maximum deflection in this opposite direction occurs as the tilt angle approaches 30°, although this maximum deflection is substantially smaller than the maximum deflection which occurs at about 17°. The nonmonotonic dependence of lateral deflection on orientation is clearly resolved. Other possible lock-in orientations at intermediate and smaller angles may be difficult to resolve in a system of the present size. In principle, transport through larger arrays of the optical tweezers 112 would reveal a more extensive hierarchy of locked-in states, possibly resembling the Devil's staircases predicted for other systems.

As explained in more detail in the Example provided hereinafter, passive optically-induced lateral deflection in accordance with the present invention has been observed in a suspension of colloidal silica spheres 1.5 μm in diameter dispersed in demonized water. A 10×10 array of the optical tweezers 112 was created with a static computer-generated diffraction grating illuminated by 73 m W of laser light at a wavelength of 532 nm in a standard holographic optical tweezer (HOT) optical train. The particles 113 were contained between parallel glass walls in a sealed sample chamber 70. Flow was induced with a pressure differential across the sample chamber 70. The particles' trajectories across the 78×53 μm² field of view were recorded on video tape before being digitized and analyzed using conventionally-known image analysis techniques.

The laterally deflected particles 113 can be collected by a variety of methods according to the present invention. These methods include the use of microfluidics channels. The particles 113 not deflected by the array, presumably because they interact less strongly with the optical traps or more strongly with the external force, will not be deflected and so will not be collected. This distinction makes possible fractionation of the particles 113 based on quite general considerations of their physical properties, with control parameters including scale, symmetry, extent, and intensity of the optical trapping arrays, and the nature and strength of the external force. In the example shown in FIGS. 2A–2D, the external force was provided by hydrodynamic drag. Further, separation of particles can be effectuated on the basis of sensitivity to driving force, laser beam intensity, and optical gradient conditions wherein particle sensitive variables are particle size, particle shape, dielectric constant, surface change density, magnetic susceptibility, nonlinear optical properties and index of refraction.

Reducing the traps' efficacy either by reducing the laser intensity or else by increasing the external driving force allows otherwise locked-in ones of the particles 113 to cross more easily from one row of the tweezers 112 to the next. This reduces the degree of mode locking for a given angle, and thus also the angle of maximum deflection and also the maximum deflection itself, until finally none remains. This threshold should be independent of the array's extent.

Loss of deflection upon depinning also provides the basis for a very general continuous fractionation technique. The particles 113 more strongly influenced by the array of the tweezers 112 could be deflected to greater angles than the particles 113 driven more strongly by the external force. Consider, for example, colloidal spheres for the particles 113 which differ only in their radii, a. The optical gradient force exerted on sub-wavelength sized spheres varies roughly as $a^3$. The well known Stokes drag, on the other hand, varies as "a". Larger spheres embodying the particles 113, therefore, are disproportionately influenced by the optical tweezers 112, while the smaller particles 113 can pass through with smaller deflection. Orienting the array 112 of the optical tweezers 112 near the angle of optimal deflection and adjusting the intensity to place the largest particles 113 in the hopping condition therefore deflects that largest fraction laterally out of the otherwise mixed flow. The deflected fraction can be collected continuously, for instance by flowing the separated fractions into separate microfluidic channels. The undeflected fraction can be further fractionated by additional stages of the optical tweezers 112 downstream of the first. These additional stages can even be integrated into a single holographic optical tweezer array with gradated characteristics.

Continuous fractionation offers obvious benefits over traditional methods such as gel electrophoresis which separate a sample's fractions along the line of the applied force and thus can only operate on a discrete amount of material at a time.

As described in the background, competition between misaligned forces has been applied to other continuous fractionation schemes, including electrophoresis through arrays of microfabricated posts and flow past dielectrophoretic Brownian ratchets created from asymmetric interdigitated electrodes. Optical fractionation offers several advantages. The array of the optical tweezers 112 can be reconfigured dynamically by varying the laser intensity and array orientation. Even the lattice constant and symmetry can be adjusted to suit the separation problem at hand. Unlike posts which present a fixed barrier to all the particles 113, the optical tweezers 112 can have markedly different influences on different materials. Choice of wavelength therefore opens up additional possibilities for continuous optical fractionation. All of these performance-determining properties, furthermore, can be varied continuously during operation. Common failure modes such as clogging similarly can be remedied by extinguishing the trap array. Also unlike systems based on microfabricated sample chambers, optical fractionation requires quite simple sample handling, all of the sorting being accomplished by patterns of light rather than by distributions of matter. Recent observations of molecular drift mediated by optical gradients allow one to conclude that fractionation based on transport through the arrays 110 of the optical tweezers 112 can apply even down to the scale of macromolecules. Straightforward consideration of the forces in the implementation of passive optically-induced lateral deflection described herein demonstrate the ability of highly selective fractionation.

Figure 6:
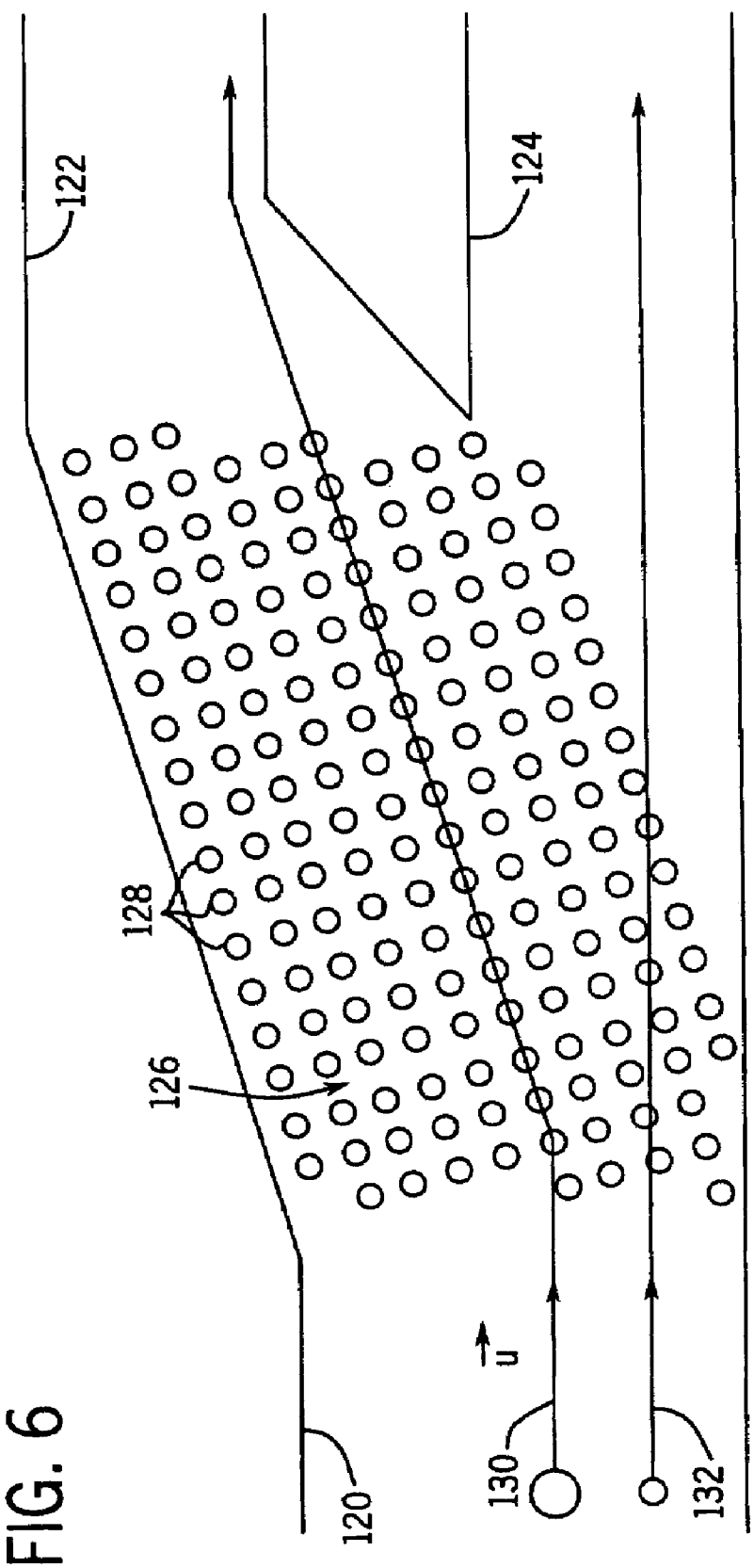
FIG. 6 is a representation of a static array of optical tweezers used in conjunction with a microfluidics channel for particle separation.

The above described principles can be used as a method for separating the particles 113 into two different flow streams. FIG. 6 shows an example of a microfluidics channel 120 that branches into a first subchannel 122 and a second subchannel 124. Before the division of the microfluidics channel 120 into the first and second subchannels 122 and 124, an array 126 of optical tweezers 128 is angularly offset relative to the flow u from an external force. In the case where a larger particle 130 and a smaller particle 132 both pass through the array 126, the larger particle 130 incurs more lateral deflection than the smaller particle 132 due to the particle's larger radius. As a result of this action, the smaller particle 132 will travel in a substantially straight line into the second subchannel 124, while the larger particle 130 will travel into the partially offset first subchannel 122.

The method of the invention can thus be used in a variety of applications. These applications include, without limitation, the separation of chromosomes, the purification of particle types and proteins, and DNA sizing. Additionally, macromolecules and nanoclusters can be manipulated in a similar manner. Furthermore, it is also possible to incorporate a number of angularly offset arrays of the tweezers 112 in series with each other. Such an arrangement allows for the further separation of the particles 113.

The following non-limiting example illustrates generally certain principals of the invention.

EXAMPLE

One preferred system, shown schematically in FIG. 1 includes 1.5 µm diameter silica spheres (Bangs Labs) dispersed in deionized water and confined to a horizontal layer 15 µm thick between parallel glass surfaces. These spheres are considerably denser than water and readily sediment into a monolayer about 2 µm above the lower wall of the sample container. The edges of the sample volume are sealed to form a flow channel. Two glass tubes bonded to holes through the upper glass wall provide access to the sample volume and serve as reservoirs for colloid, water and clean mixed-bed ion exchange resin. The ends of the tubes are connected to continuous flows of humidified Ar gas. Blocking one of the flows causes a pressure imbalance which drives colloid through the sample chamber and past the 75×58 µm$^2$ field of view of a 100×NA 1.4 oil-immersion objective mounted on an Olympus IMT-2 microscope base. By controlling the flow of Ar, we can induce colloid to travel at up to 100 µm/sec over periods of an hour or more.

The individual spheres' in-plane motions are tracked with a resolution of 10 nm at 1/60 sec intervals using precision digital video microscopy. The resulting trajectory data allow us to monitor the spheres' progress through potential energy landscapes that we create with light.

Our optical potential landscapes are based on the holographic optical tweezer technique in which a single beam of light is formed into arbitrary configurations of optical traps using a computer-generated diffractive beam splitter. Each beam created by this diffractive optical element (DOE) is focused by the objective lens into a diffraction-limited spot capable of stably trapping one of the silica spheres. While holographic optical tweezers can be arranged arbitrarily in three dimensions, we chose a planar 10×10 square array with 2.4 µm lattice constants to model the free energy modulations typically discussed in theoretical and numerical treatments of analagous physical systems. The traps are focused into the plane of the monolayer to avoid displacing spheres vertically as they flow past.

If the Stokes drag due to the flowing fluid greatly exceeds the optical tweezers' maximum trapping force, then colloidal particles flow past the array with their trajectories unperturbed. Conversely, if the trapping force dominates, then particles fall irreversibly into the first traps they encounter. Our observations are made under intermediate conditions for which trapping and viscous forces are nearly matched. Under these conditions, the trapping array's influence on a particle's trajectory depends on its orientation with respect to the flow. In symmetry-hindered directions for which the trapping force exceeds viscous drag, the flow still can push a particle far enough to the edge of an individual trap that it can make a thermally-assisted jump to the next well. Lower potential barriers in symmetry-favored directions may only modulate the speed of a passing particle. A particle hopping from well to well under these circumstances chooses a path through the potential energy landscape based on a tradeoff between geometric proximity and energetic expediency. These tradeoffs lead to interesting kinetic transitions as the driving force's relationship to the trapping potential changes.

Our silica spheres enter the hopping state for flow speeds of 30±3 µm/sec and laser intensities of 100±10 µW/trap. The real density of spheres in the minelayer is low enough that no more than 5% of the traps are occupied at any time. While collisions sometimes occur between hopping particles, they are comparatively rare. The data shown in FIGS. 2A–2D were obtained in this manner.

While preferred embodiments of the invention have been shown and described, it will be clear to those skilled in the art that various changes and modifications can be made without departing from the invention in its broader aspects.

What is claimed is:

1. An apparatus for controlled deflection of particles, comprising:
    a plurality of particles;
    an external bias force from a bias force source applied to the plurality of particles; and
    an optical tweezer array having optical gradient forces associated therewith and the optical array oriented at a tilt angle relative to a direction of the bias force generated by the bias force source whereby the optical gradient forces of the optical tweezer array interact with the bias force to deflect the plurality of particles.

2. The apparatus as defined in claim 1 wherein the external bias force from the bias source and the optical tweezer array and the associated optical gradient forces are adjustable to a change in amount and direction of deflection of selected ones of the plurality of particles.

3. The apparatus as defined in claim 2 further including a diffractive optical element to generate the optical tweezer array, the diffractive optical element rotated by an angle to rotate the optical tweezer array with respect to flow direction of the plurality of particles, thereby enabling selected change of amount of deflection for the particles.

4. The apparatus as defined in claim 3 wherein the diffractive optical element is rotated to a particular range of angles which cause the plurality of particles to be deflected away from direction of flow of the particles.

5. The apparatus as defined in claim 3 wherein retrograde deflection with respect to the angle of rotation is achieved by means of generating a different local potential energy landscape of the optical tweezer array at selected angles of rotation for the diffractive optical element.

6. The apparatus as defined in claim 5 wherein the different local potential energy landscape causes formation of threshold angles of rotation of the optical tweezer array, thereby achieving locked in trajectories of the particles.

7. The apparatus as defined in claim 6 wherein a hierarchy is established to provide a form of Devil's staircase of plateaus in transverse transport of the particles with increasing angle of rotation of the diffractive optical element.

8. The apparatus as defined in claim 2 wherein transverse deflection of the particles undergoes a change of sign with changing the angle of rotation of the optical tweezer array.

9. The apparatus as defined in claim 1 achieves the plurality of particles comprises different types of particles which respond differently to the optical tweezer array and the external bias force, thereby enabling sorting of the different type of particles.

10. The apparatus as defined in claim 1 wherein a continuous source of the plurality of particles is provided and continuous fractionated portions are produced.

11. The apparatus as defined in claim 1 further including means to monitor clogging of the apparatus and to remedy clogging by extinguishing the optical tweezer array.

12. The apparatus as defined in claim 1 further including a plurality of microfluidic channels disposed to collect the individual particle flow channels created by control of the optical array of the flow of particles created by the bias force from the bias force source.

\* \* \* \* \*